United States Patent [19]

Cunningham

[11] 4,286,594
[45] Sep. 1, 1981

[54] APPLICATOR AND TAMPON

[76] Inventor: Thomas W. Cunningham, 3580 Emerwood La., Orlando, Fla. 32806

[21] Appl. No.: 96,431

[22] Filed: Nov. 21, 1979

Related U.S. Application Data

[63] Continuation-in-part of Ser. No. 43,231, May 29, 1979.

[51] Int. Cl.³ .............................................. A61F 15/00
[52] U.S. Cl. .................................................... 128/263
[58] Field of Search ............... 128/756, 759, 263, 269, 128/285, 271

[56] References Cited

U.S. PATENT DOCUMENTS

| | | | |
|---|---|---|---|
| 2,105,710 | 1/1938 | Wadel | 128/271 |
| 2,401,585 | 6/1946 | Seidler | 128/263 |
| 2,413,480 | 12/1946 | Winter | 128/263 |
| 2,922,423 | 1/1960 | Rickard et al. | 128/263 |
| 3,358,686 | 12/1967 | Asaka | 128/263 |
| 3,499,447 | 3/1970 | Mattes et al. | 128/263 |
| 3,674,025 | 7/1972 | Bleuer | 128/263 |
| 3,749,093 | 7/1973 | Bloom | 128/263 |
| 4,211,225 | 7/1980 | Sibalis | 128/285 |

FOREIGN PATENT DOCUMENTS 2406823  8/1975  Fed. Rep. of Germany ........... 128/263

Primary Examiner—C. Fred Rosenbaum
Attorney, Agent, or Firm—Duckworth, Hobby, Allen, Dyer & Pettis

[57] ABSTRACT

An applicator for a member having a surface, such as a tampon, includes a flexible applicator along the surface with the applicator having a convolution so as to double the applicator upon itself to form parallel walls with the convolution therebetween. The surface of the member may be exposed by relative movement of one of the walls of the applicator with respect to the member. In one embodiment, the applicator sleeve is provided with a slit extending to one end permitting the sleeve to be rolled along a direction substantially parallel with the central axis of the member, and may include an opposing second slit at the other end facilitating a pushing movement of the member through the sleeve.

14 Claims, 6 Drawing Figures

APPLICATOR AND TAMPON

This application is a continuation-in-part of application, Ser. No. 43,231, filed May 29, 1979.

BACKGROUND OF THE INVENTION

1. Field of the Invention:

The present invention relates to applicators.

2. Description of the Prior Art:

During the menstruation cycle, women customarily insert an oblong porous object customarily referred to as a tampon into the vagina to absorb discharge fluids from the body. During the insertion process, the body muscles tend to contract, thus making entry of the tampon uncomfortable.

There have been numerous tampon wrappings and applicators devised in the prior art to attempt to avoid this discomfort.

In U.S. Pat. No. 3,749,093, Bloom discloses an insertable device package for tampons, in which the insertion device comprises an elongated sheath having a pair of side walls separated by a convolution, the tampon being inserted by pushing along the bottom thereof to force the tampon through one end, causing the convolution to roll inwardly, extending the inner sidewall during the insertion process.

In U.S. Pat. No. 2,922,422, Bletzinger discloses a cellulose outer shell as an applicator for a tampon. Similar arrangements are disclosed in U.S. Pat. No. 2,922,423 to Richard, et al, and U.S. Pat. No. 3,499,447 to Mattes, et al.

Crockford, in U.S. Pat. No. 3,058,469, and Kobler, et al, in U.S. Pat. No. 3,135,262 both disclose a protective sheath that may be folded back during insertion of the tampon. Asaka, in U.S. Pat. No. 3,358,636, discloses an insertion mechanism.

Other prior art of interest includes U.S. Pat. No. 3,068,867 to Bletzinger et al., which discloses the use of an insertion rod and a withdrawal string. See also U.S. Pat. No. 4,048,998 to Nigro, disclosing a tampon inserter.

SUMMARY OF THE INVENTION

The present invention contemplates an applicator for a member comprising the member having a surface, with a flexible applicator along the surface and having a convolution so as to double the applicator upon itself to form parallel walls with the convolution therebetween. The surface of the member may be exposed by relative movement of one of the walls of the applicator with respect to the member. In a specific arrangement, the member is enclosed inside a flexible applicator sleeve with the convolution along the sleeve, permitting the sleeve to be rolled along a direction substantially parallel with a central axis of the member.

A preferred embodiment of the present invention contemplates an applicator and tampon, in which the tampon is formed of an oblong absorbent member having a central axis and a forward end adapted to be extended first into the vagina. A flexible applicator sleeve is fitted about the tampon and overlapping a portion of the forward end of the tampon, with a convolution along the sleeve permitting the sleeve to be rolled along a direction substantially parallel with the central axis during or after movement of the tampon into the vagina. For these purposes, the term "convolution" means a single roll, with a portion of the sleeve about another portion of the sleeve.

In one embodiment of the present invention, the flexible applicator sleeve surrounds the tampon and has a longitudinal slit. The slit extends from one end of the tampon to one extremity of the sleeve, and may preferably have perforations along the line which is aligned with the slit, but adjacent the tampon. The sleeve may be fitted with a second slit extending from the other extremity of the sleeve, the second slit being out of alignment with the first slit. In use, the first slit permits the sleeve to be rolled backward substantially parallel with the central axis of the tampon to form the convolution, and thereafter facilitate relative movement of the tampon with respect to the sleeve. In this regard, the conventional stick or similar means may be used to push the tampon upward, opens the distal end of the sleeve to permit access to the tampon.

THE DRAWING

DETAILED DESCRIPTION OF THE PREFERRED EMBODIMENT

Figure 1:
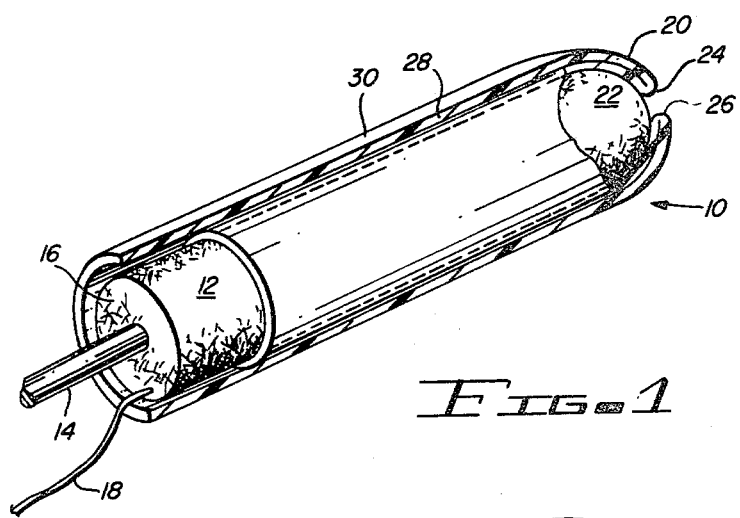
FIGS. 1, 2 and 3 illustrate one embodiment of the present invention and the consecutive steps in the use of that embodiment.

An applicator and tampon in accordance with the present invention and its manner of intended use will now be described with reference to FIGS. 1, 2 and 3.

The applicator and tampon, referred to generally by the reference numeral 10, includes a tampon 12 comprising an absorbent fiber body, which is compressed to such an extent that it is substantially stable under normal atmospheric conditions but expands when wetted as during its intended use. The tampon 12 is provided with a conventional insertion rod 14 which may comprise wood, paper or any other material of a suitable nature, and which is appropriately joined at the distal end 16 of the tampon 12. The applicator and tampon is further provided with a conventional withdrawal string 18 suitably anchored to the tampon 12 and exits adjacent to the distal end 16.

The applicator, referred to generally by the reference numeral 20, comprises a flexible sleeve about the tampon and overlapping a portion of the forward end 22 of the tampon 12. A suitable material for use as the sleeve 20 may be, for example, polyethylene or polypropylene or other material having sufficient flexibility to form the desired convolution.

The sleeve 20 is wrapped about the tampon 12 in such a manner as to form a convolution 24 toward the forward end 22 of the tampon 12, the convolution forming an opening 26 axial with the central axis of the tampon 12 and overlapping the forward end 22. The convolution 24 thus separates the sleeve 20 into two sidewalls 28 and 30, the first sidewall 28 being next adjacent to the tampon 12, and the outer sidewall 30 being next adjacent to the first wall 28.

The manner in which the applicator and tampon 10 is employed will now be described with reference to FIGS. 2 and 3.

Figure 2:
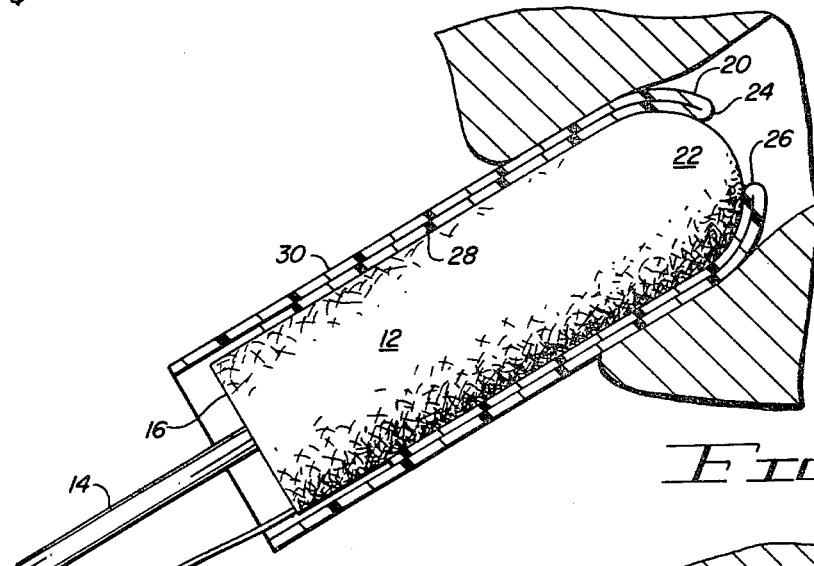
Figure 3:
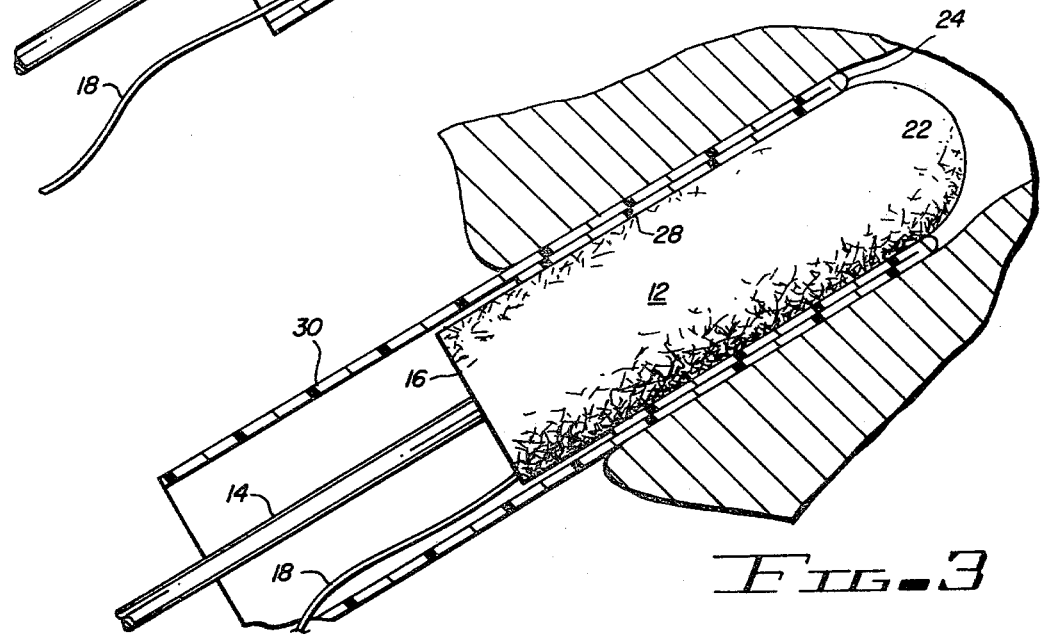

Noting FIG. 2, the applicator and tampon 10 are inserted into the vagina, with the muscle tissue coming in contact with the outer wall 30 of the sleeve 20. As the tampon 12 is forced into the vagina by application of pressure on the insertion rod 14, the sleeve 20 rolls at the convolution 24, with the outer wall 30 remaining substantially stationary. After the tampon is inserted in the desired manner, the insertion rod 14 may be removed in a conventional fashion by rotation thereof, and the sleeve 20 may be removed by simply pulling the outer extremity of the outside wall 30 away from the vagina. Alternatively, the tampon 12 is placed into position and the sleeve 20 is removed while the tampon remains relatively stationary. It will thus be seen that a tampon and applicator constructed in accordance with the present invention reduces significantly the amount of tampon insertion discomfort. Further, the use of the thin poly-resin sleeve 20 provides relatively easy entry during the insertion process.

It will be understood that the sleeve 20 may be coated with an appropriate lubricant. It will be further understood that the sleeve 20 may be adapted for use with tampons of different sizes and configurations, i.e., rectangular or other shapes.

While the applicator has been described above for use with tampons, it will be understood that the applicator may be employed with other products as well.

A second embodiment of the applicator and tampon in accordance with the present invention will now be described with reference to FIGS. 4, 5, and 6. The combination applicator and tampon, referred to generally by the reference number 50, includes a tampon 52 having a longitudinal central axis. The tampon 52 includes a conventional insertion rod 54 and a withdrawal string 58 suitably anchored to the tampon 52 adjacent the distal end thereof. The applicator, referred to generally by the reference numeral 60, comprises a flexible sleeve about the tampon 52 and overlapping the forward and rearward ends of the tampon.

Figure 4:
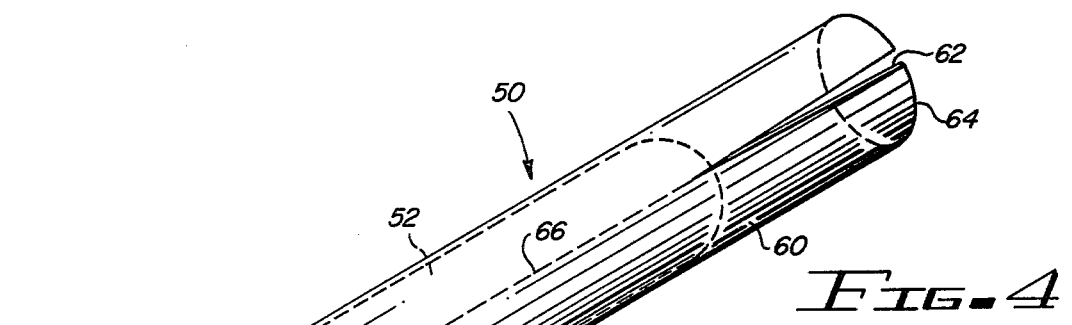
FIGS. 4, 5 and 6 illustrate consecutive steps in the use of another embodiment of the applicator and tampon of the present invention.

As is clearly shown in FIG. 4, the applicator sleeve 60 surrounds the tampon 52 and has a longitudinal slit 62 along a portion thereof substantially parallel with the central axis of the tampon. This slit 62 extends from one end of the tampon 52 through the forward extremity 64 of the sleeve 60. With continuous reference to FIG. 4, the sleeve 60 further includes a perforated line 66 which is aligned with the slit 62 adjacent the tampon 52. The applicator sleeve 60 of FIGS. 4, 5, and 6 further preferably include a second slit 68 in the sleeve extending from the other extremity 70, the slit being out of alignment with the first slit 62. In the embodiment shown in FIG. 4, second slit 68 is out of alignment with slit 62 by 180°. However, it will be understood that the second slit 68 need not necessarily be parallel with the central axis of the tampon 52, but preferably is so parallel with that axis.

The mode of operation of the applicator and tampon 50 of FIGS. 4, 5, and 6 will now be described with reference to FIGS. 5 and 6.

Figure 5:
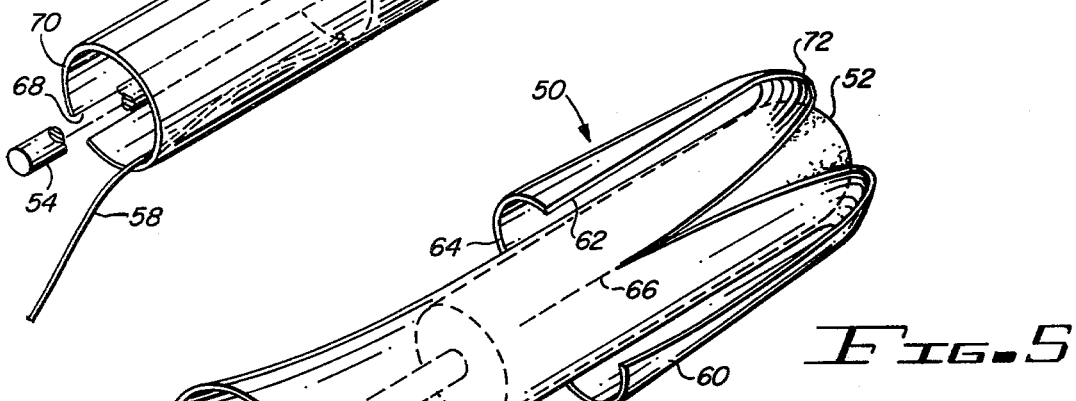

First, note in FIG. 5, the applicator sleeve 60 is initially folded back along the convolution 72 adjacent the forward extremity of the tampon 52, and the tampon and applicator combination 50 has been inserted. As is shown in FIG. 6, the insertion rod 54 is then pushed forward, causing the tampon 52 to move forward into the appropriate position in the vagina. The use of the insertion rod 54 (or other means, such as the user's finger) is facilitated by the wider opening at the distal extremity 70 of the sleeve 60, effectuated by the second slit 68. The sleeve 60 may then be removed along with the insertion rod 54.

Figure 6:
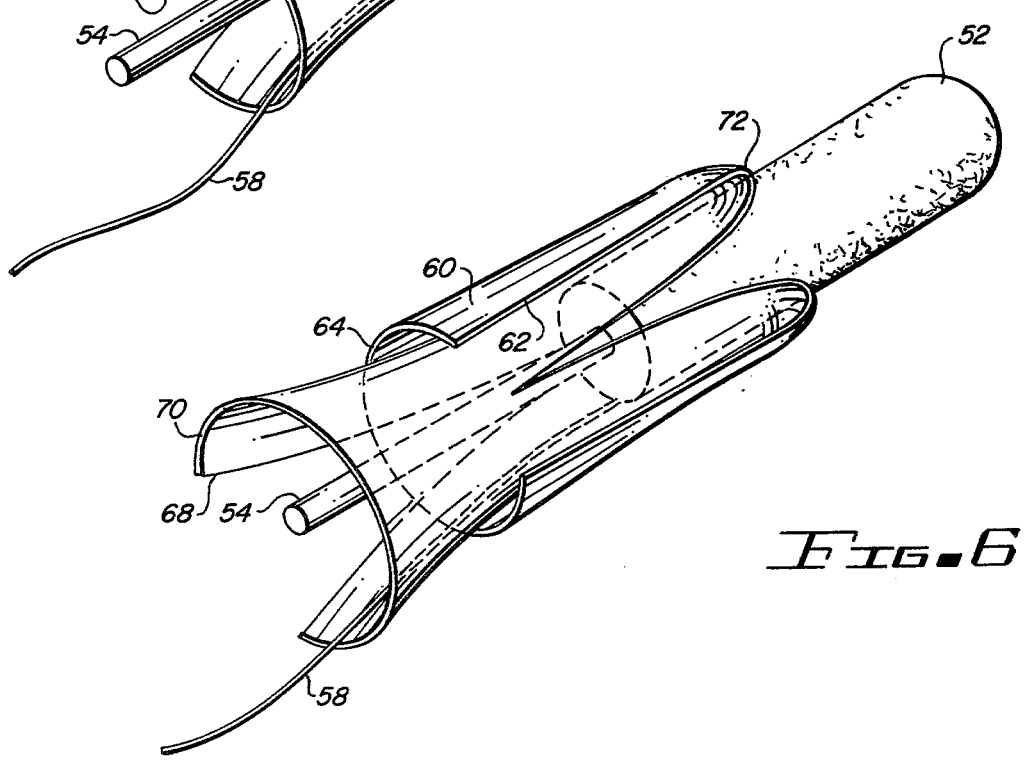

While the second embodiment of FIGS. 4, 5 and 6 has been disclosed as including both first and second slits 62 and 68, as well as a perforated line 66, it will be appreciated by those skilled in the art that the arrangement here disclosed may include only the first or second slit alone or in combination with the perforated line 66.

I claim:
1. An applicator and member comprising:
   (a) an oblong member having a longitudinal central axis;
   (b) a flexible applicator sleeve surrounding said member and having a longitudinal slit along a portion thereof and substantially parallel with said central axis of said member; and
   (c) a convolution along said portion of said sleeve, said portion having a sufficient length to extend rearward from said convolution to the end of said member opposite said convolution, permitting said portion of said sleeve to be grasped and to be rolled at said convolution along a direction substantially parallel with said central axis.
2. The applicator and member recited in claim 1 wherein said slit in said portion of said sleeve extends from one end of said member to one extremity of said sleeve.
3. The applicator and member recited in claim 1 further comprising said sleeve having perforations therein along a line which is aligned with said slit in said portion of said sleeve.
4. The applicator and member recited in claim 1 further comprising a second slit in said sleeve extending from the other extremity, said second slit being out of alignment with said first slit.
5. The applicator and member recited in claim 4 wherein said second slit is substantially parallel with said central axis of said member.
6. The applicator and member recited in claim 1 wherein said sleeve comprises a poly-resinous material.
7. The applicator and member recited in claim 1 wherein said member comprises a tampon.
8. A tampon and applicator therefor, comprising:
   (a) a tampon formed of an oblong absorbent member having a central axis and a forward end adapted to be inserted first into the vagina;
   (b) a flexible applicator sleeve around and substantially longer than said tampon, and having a slit along at least a portion of said sleeve and being substantially parallel with said central axis, said slit extending away from said forward end of said tampon to the extremity of said sleeve; and wherein
   (c) said portion of said sleeve beyond said forward end is adapted to be folded back along the remainder of said sleeve to thereby form a convolution along said sleeve, permitting said sleeve to be removed from said tampon by relatively low-friction motion between said tampon and sleeve during insertion of said tampon.
9. The tampon and applicator recited in claim 8 further comprising said sleeve having perforations therein along a line which is aligned with said slit in said portion of said sleeve.
10. The tampon and applicator recited in claim 8 further comprising a second slit in said sleeve extending from the other extremity, said second slit being out of alignment with said first slit.
11. The tampon and applicator recited in claim 10 wherein said second slit is substantially parallel with the central axis of said member.

12. The applicator and member recited in claim 10 wherein said sleeve comprises a poly-resinous material.

13. A tampon and applicator as recited in claim 8 further comprising an insertion rod joined with the distal end of said tampon.

14. A tampon and applicator as recited in claim 8 further comprising a withdrawal string joined to said tampon adjacent the distal end thereof.

* * * * *